(12) United States Patent
DuPont et al.

(10) Patent No.: US 11,771,578 B1
(45) Date of Patent: Oct. 3, 2023

(54) CROSS-STRAP TENSIONING APPARATUS FOR OSTEOARTHRITIS BRACES

(71) Applicant: Townsend Industries, Inc., Bakersfield, CA (US)

(72) Inventors: Marie Camille DuPont, Bakersfield, CA (US); John Patrick Martin, Oceanside, CA (US)

(73) Assignee: Townsend Industries, Inc., Bakersfield, CA (US)

( * ) Notice: Subject to any disclaimer, the term of this patent is extended or adjusted under 35 U.S.C. 154(b) by 0 days.

(21) Appl. No.: 17/913,759

(22) PCT Filed: May 10, 2022

(86) PCT No.: PCT/US2022/028587
§ 371 (c)(1),
(2) Date: Sep. 22, 2022

(87) PCT Pub. No.: WO2022/265735
PCT Pub. Date: Dec. 22, 2022

Related U.S. Application Data

(60) Provisional application No. 63/210,911, filed on Jun. 15, 2021.

(51) Int. Cl.
*A61F 5/01* (2006.01)

(52) U.S. Cl.
CPC .... *A61F 5/0123* (2013.01); *A61H 2201/1642* (2013.01)

(58) Field of Classification Search
CPC ...... A61F 5/0123; A61F 5/0109; A61F 5/013; A61F 5/0102; A61F 5/01; A61F 5/0125;

(Continued)

(56) References Cited

U.S. PATENT DOCUMENTS

| 4,425,912 A | 1/1984 | Harper |
| 4,805,606 A | 2/1989 | McDavid, III |

(Continued)

FOREIGN PATENT DOCUMENTS

| WO | 2018104316 A1 | 6/2018 |
| WO | 2019101910 A1 | 5/2019 |
| WO | 2021158715 A1 | 8/2021 |

OTHER PUBLICATIONS

International Search Report and Written Opinion, PCT/US2022/028587, dated Jul. 20, 2022.

*Primary Examiner* — Alireza Nia
*Assistant Examiner* — Daniel A Miller
(74) *Attorney, Agent, or Firm* — MASTER KEY IP, LLP; Justin G. Sanders

(57) ABSTRACT

A cross-strap tensioning apparatus is disclosed for use with a brace having a proximal portion engageable above a joint of a user and an opposing distal portion engageable below the joint. In at least one embodiment, the apparatus provides first and second cross-straps each extending between and interconnecting the proximal and distal portions of the brace. A terminal end of each of a first anterior strap portion and a spaced apart first posterior strap portion of the first cross-strap, along with a second anterior strap portion and a spaced apart second posterior strap portion of the second cross-strap, provides a cord channel configured for allowing a cord from a tensioning mechanism to extend therethrough in series. During use, as the tensioning mechanism is selectively tightened, the cord urges each of the first anterior strap portion, first posterior strap portion, second anterior strap portion and second posterior strap portion closer together.

20 Claims, 6 Drawing Sheets

(58) Field of Classification Search
CPC ...... A61F 5/0118; A61F 5/022; A61F 5/0106;
A61F 5/24; A61F 5/00; A61F 2005/0137;
A61F 2005/0179; A61F 2005/0144; A61F
2005/0139; A61F 2005/0181; A61F
2005/0174; A61F 2005/0134; A61F
2005/0172; A61F 2210/0057; A61F
5/0104; A61F 5/0111; A61F 5/0127;
A61F 5/0195; A61H 2201/1642; A61H
2201/1602; A61H 2201/164; B25J
9/0006; A43C 11/165; A43C 7/08; A43C
1/003; A43C 1/006
USPC .......................................................... 602/26
See application file for complete search history.

(56) References Cited

U.S. PATENT DOCUMENTS

| | | |
|---|---|---|
| 5,016,621 A | 5/1991 | Bender |
| 5,857,989 A | 1/1999 | Smith, III |
| 7,198,610 B2 | 4/2007 | Ingimundarson et al. |
| 7,597,675 B2 | 10/2009 | Ingimundarson et al. |
| 7,662,122 B2 | 2/2010 | Sterling |
| 8,016,781 B2 | 9/2011 | Ingimundarson et al. |
| 8,231,560 B2 | 7/2012 | Ingimundarson et al. |
| 8,808,211 B2 | 8/2014 | Paulos et al. |
| 8,858,482 B2 | 10/2014 | Ingimundarson et al. |
| 8,864,692 B2 | 10/2014 | Ingimundarson et al. |
| 9,265,645 B2 | 2/2016 | Ingimundarson et al. |
| 9,358,146 B2 | 6/2016 | Thorsteinsdottir et al. |
| 9,895,250 B2 | 2/2018 | Thorsteinsdottir et al. |
| 10,285,840 B2 | 5/2019 | McRae |
| D854,173 S | 7/2019 | Violeau et al. |
| 2005/0273025 A1 | 12/2005 | Houser |
| 2007/0049857 A1 | 3/2007 | Quinn et al. |
| 2013/0144197 A1 | 6/2013 | Ingimundarson et al. |
| 2014/0358054 A1 | 12/2014 | Capra et al. |
| 2015/0290013 A1 | 10/2015 | Mueller et al. |
| 2017/0105865 A1 | 4/2017 | Gildersleeve et al. |
| 2017/0189218 A1 | 7/2017 | Paulos et al. |
| 2019/0240054 A1 | 8/2019 | Paulos et al. |
| 2019/0350735 A1 | 11/2019 | Ingimundarson et al. |
| 2020/0305555 A1* | 10/2020 | Yamamoto ............ A43C 11/165 |
| 2021/0022900 A1* | 1/2021 | Hebenstreit ........... A61F 5/0106 |

* cited by examiner

CROSS-STRAP TENSIONING APPARATUS FOR OSTEOARTHRITIS BRACES

RELATED APPLICATIONS

This application is a 35 U.S.C. § 371 US national stage entry and is entitled to the earliest effective filing date of international application number PCT/US2022/028587, filed on May 10, 2022, which itself claims priority to U.S. provisional application Ser. No. 63/210,911, filed on Jun. 15, 2021. The contents of the aforementioned applications are incorporated herein by reference.

BACKGROUND

The subject of this provisional patent application relates generally to osteoarthritis braces, and more particularly to a cross-strap tensioning apparatus for an osteoarthritis brace configured for joining a pair of cross-straps of the brace, opposite a hinge of the brace, and allowing for independent movement of the cross-straps while maintaining a load directly across a center of the user's joint during movement of the joint.

Applicant hereby incorporates herein by reference any and all patents and published patent applications cited or referred to in this application.

By way of background, braces are widely used to treat a variety of infirmities, including osteoarthritis. Such braces may be configured to impart forces or leverage on the limbs surrounding a joint in order to relieve compressive forces within a portion of the joint, or to reduce the load on the joint. Moreover, in the event that ligaments are weak and infirm, a brace may stabilize, protect, support, or rehabilitate the joint.

The knee is known to be one of the weakest joints in the body. Knee instability arising out of cartilage damage, ligament strain and other causes is relatively commonplace since the knee joint is subjected to significant loads during the course of almost any kind of physical activity requiring the use of the legs. One type of knee infirmity that many individuals are prone to having is unicompartmental osteoarthritis. Unicompartmental osteoarthritis may arise when there is a persistent uneven distribution of pressure in one of the medial and lateral compartments of the knee. Knee bracing is useful to provide compartment pain relief by reducing the load on the compartment through the application of an opposing external valgus or varus moment about the knee joint. Unloading knee braces have been shown to significantly reduce osteoarthritis knee pain while improving knee function.

There are many known unloading knee braces. Typically, braces of this type are designed to apply a moment about the knee through two mechanisms. The first mechanism is through the angulations of hinge components which induce a bending moment at a hinge. The second mechanism is provided by a three-point bending system via a pair of force straps that spirals around the knee while crossing over one another, applying a force to a prescribed aspect of the knee. However, it has been found that if more unloading of the knee is required by the brace than is obtained from normal strap tension, and if the force straps are further tightened, the knee is drawn towards the hinge and might strike the hinge. This results in the hinge applying forces to the knee that counteract the force applied by the force straps. In turn, the additional tightening of the force straps is mitigated or negated by the force exerted onto the knee from the hinge. Additionally, while some amount of movement from the force straps can be beneficial, it has been found that the force straps have a tendency to unintentionally move too far out of position, slipping above, below or to the side of the knee. Thus, there remains a need for an apparatus capable of allowing the independent movement of the force straps while maintaining a load directly across the center of the knee joint during gait.

Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing a cross-strap tensioning apparatus for use with a brace having a proximal portion engageable above a joint of a user and an opposing distal portion engageable below the joint. In at least one embodiment, the apparatus provides first and second cross-straps each extending between and interconnecting the proximal and distal portions of the brace, the first and second cross-straps substantially transversely oriented relative to one another and positioned for intersecting one another in an overlapping fashion at a cross-strap intersection substantially at the joint. The first cross-strap provides a first anterior strap portion and a first posterior strap portion spaced apart from the first anterior strap portion, while the second cross-strap provides a second anterior strap portion and a second posterior strap portion spaced apart from the second anterior strap portion. A tensioning mechanism is configured for selectively urging each of the first anterior strap portion, first posterior strap portion, second anterior strap portion and second posterior strap portion closer together. A terminal end of each of the first anterior strap portion, first posterior strap portion, second anterior strap portion and second posterior strap portion provides a cord channel configured for allowing a cord from the tensioning mechanism to extend therethrough in series. Accordingly, during use of the apparatus, as the tensioning mechanism is selectively tightened, the cord urges each of the first anterior strap portion, first posterior strap portion, second anterior strap portion and second posterior strap portion closer together.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
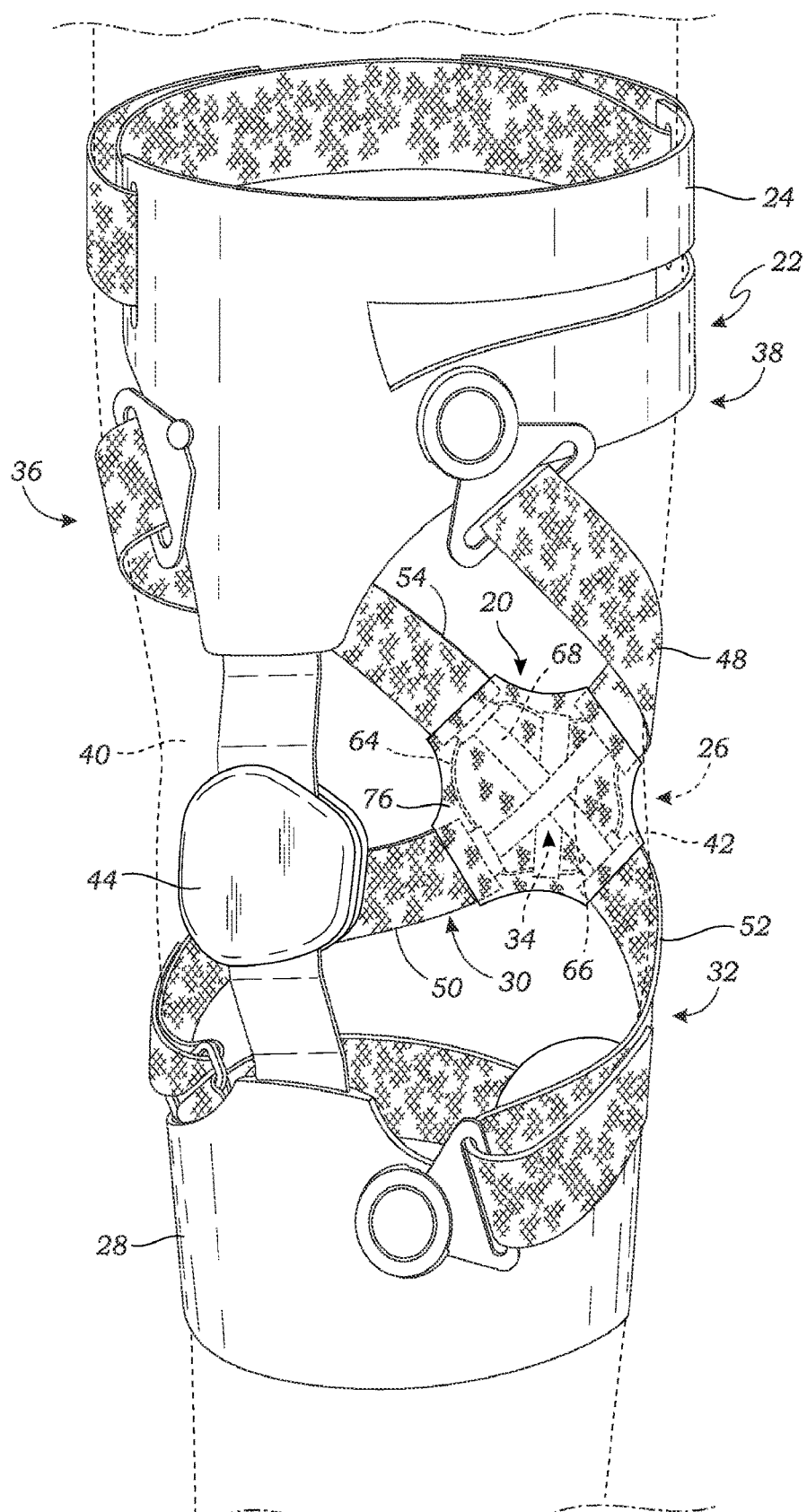
FIGS. 1 and 2 are perspective views of an exemplary cross-strap tensioning apparatus engaged with an exemplary osteoarthritis brace, in accordance with at least one embodiment.
Figure 2:
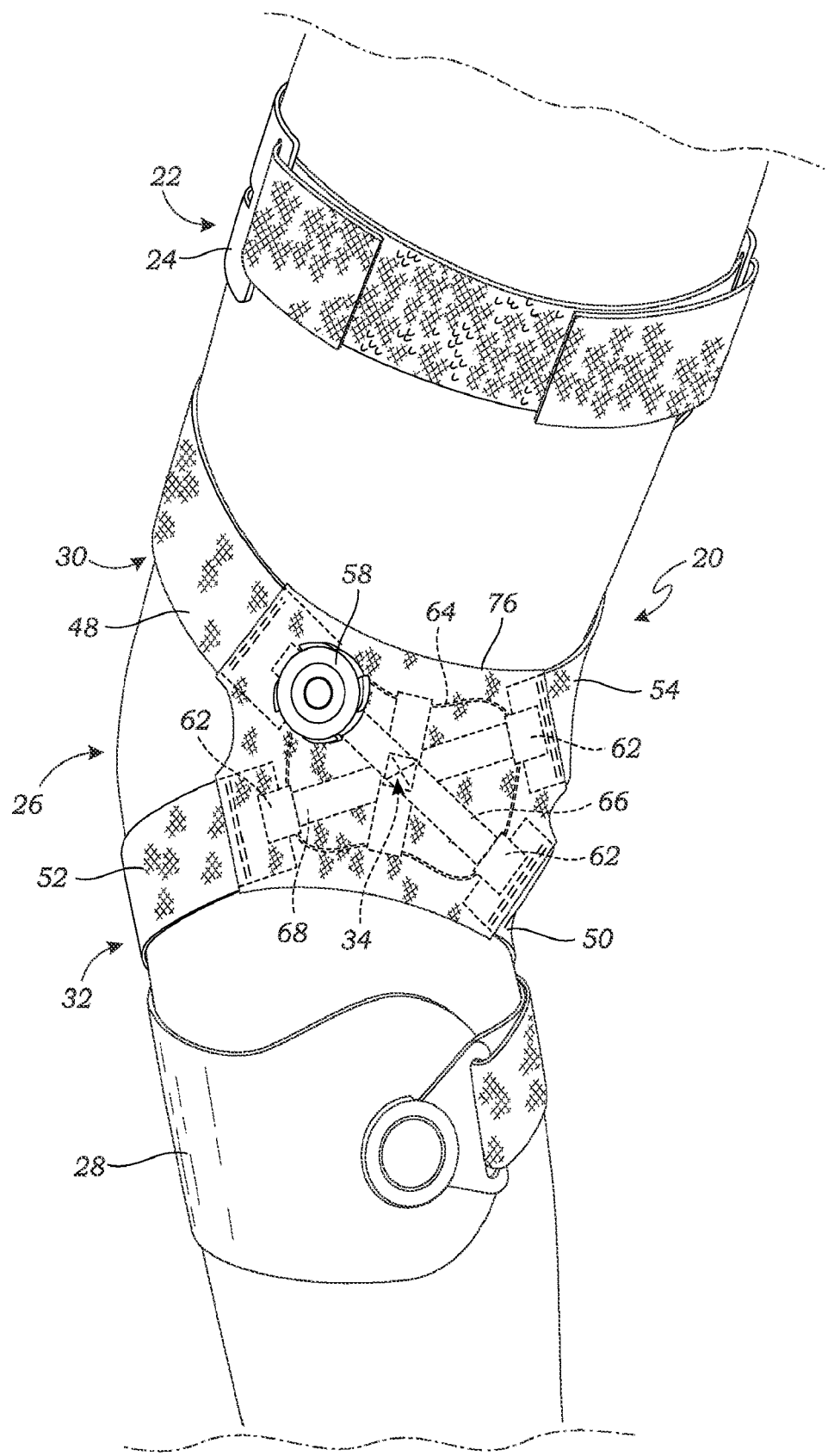

Turning now to FIGS. 1 and 2, there are shown perspective views of an exemplary embodiment of a cross-strap tensioning apparatus 20 engaged with an exemplary osteoarthritis brace 22. At the outset, it should be noted that while the apparatus 20 is discussed herein in the context of a knee brace in at least one embodiment, in further embodiments, the apparatus 20 may be utilized in combination with any other type of brace (i.e., knee brace, elbow brace, hip brace, ankle brace, spinal brace etc.) now known or later developed, so long as said braces are configured for utilizing a pair of cross-straps. Thus, use of the present invention should not be read as being limited to only knee braces, nor even the specific brace 22 that is depicted in the drawings for illustrative purposes.

With continued reference to FIGS. 1 and 2, in at least one embodiment, the exemplary brace 22 itself provides a proximal portion 24 configured for being engaged above a joint 26 of the user (such as a knee, for example), and an opposing distal portion 28 configured for being engaged below the user's joint 26. In at least one embodiment, the apparatus 20 provides an at least one first cross-strap 30 and an at least one second cross-strap 32 each extending between and interconnecting the proximal and distal portions 24 and 28 of the brace 22. In at least one embodiment, each of the at least one first cross-strap 30 and second cross-strap 32 is removably engaged with the proximal and distal portions 24 and 28 of the brace 22. In at least one alternate embodiment, each of the at least one first cross-strap 30 and second cross-strap 32 is permanently engaged with the proximal and distal portions 24 and 28 of the brace 22. In at least one embodiment, the at least one second cross-strap 32 is substantially transversely oriented relative to the first cross-strap 30 and positioned for intersecting the first cross-strap 30 in an overlapping fashion at a cross-strap intersection 34 substantially at the user's joint 26. In at least one embodiment, the first and second cross-straps 30 and 32 are positioned on either a lateral side 36 or a medial side 38 of the brace 22, such that the cross-strap intersection 34 is substantially in contact with a lateral side 40 or medial side 42 of the user's joint 26. In at least one such embodiment, the brace 22 may further provide a hinge 44 extending between the proximal and distal portions 24 and 28 and positioned on the other of the lateral or medial side 40 or 42 of the user's joint 26, opposite the cross-strap intersection 34.

Figure 3:
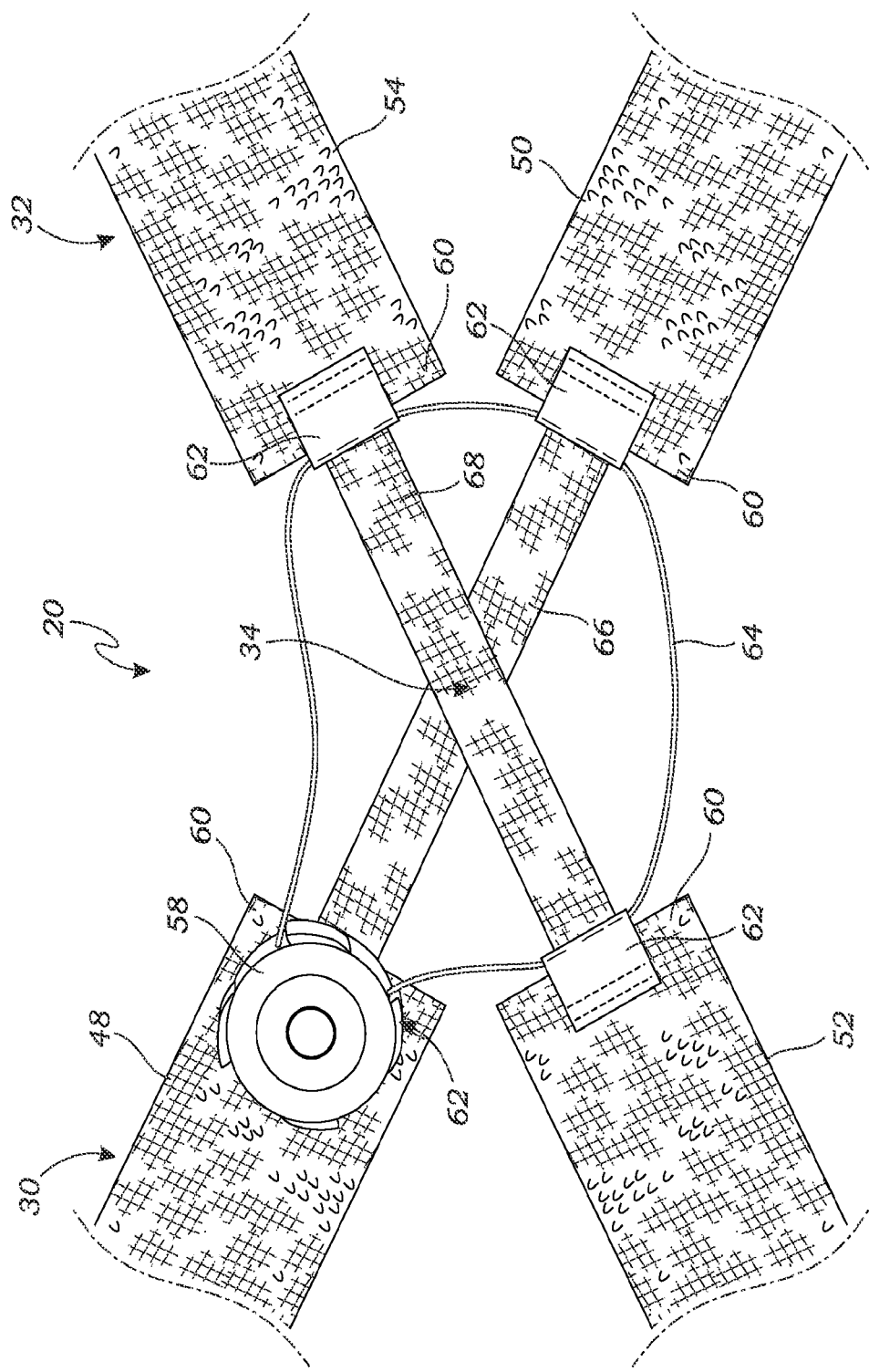
FIG. 3 is a partial top plan view of a pair of exemplary cross-straps of the apparatus, in accordance with at least one embodiment.
Figure 4:
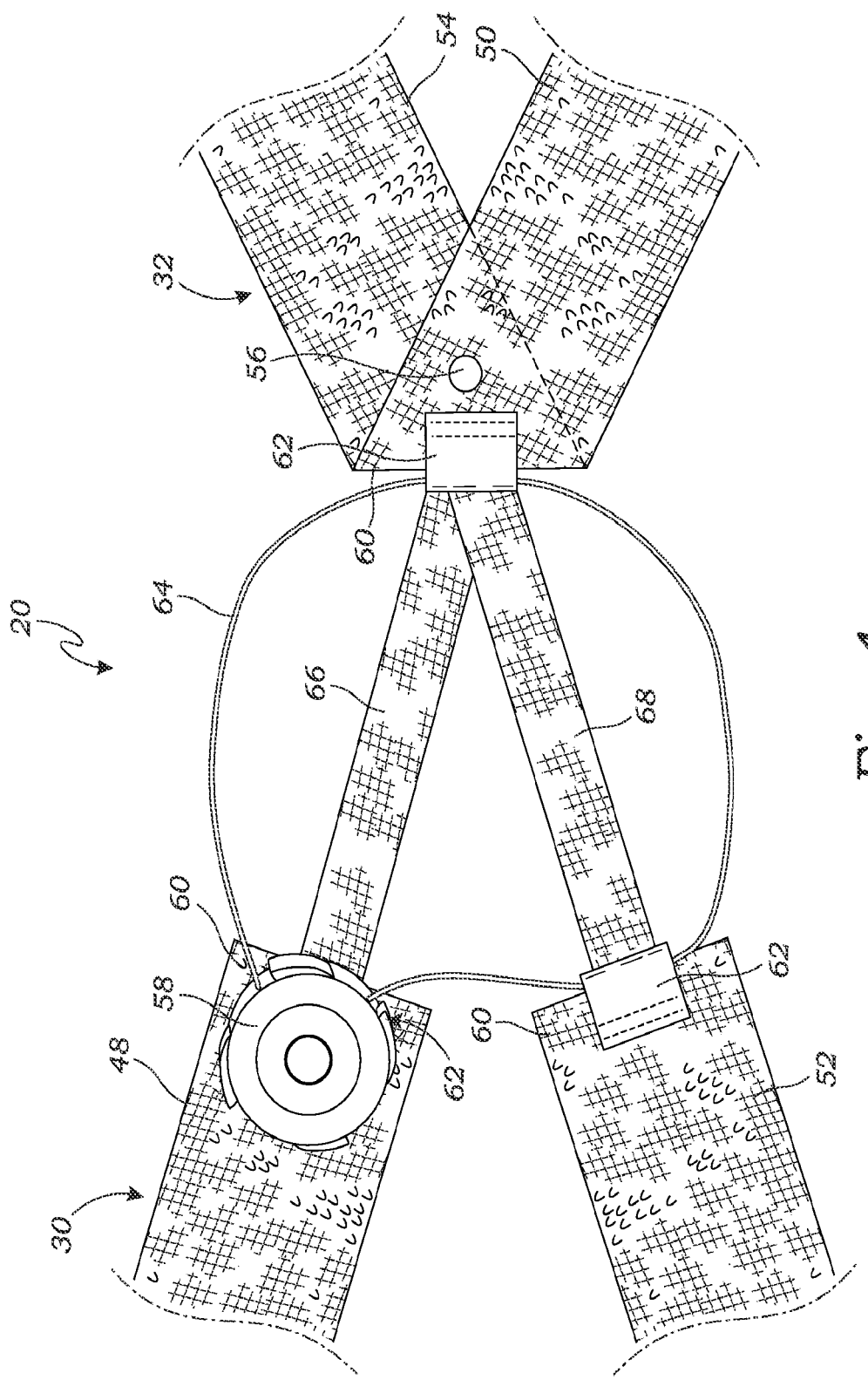
FIG. 4 is a partial top plan view of a pair of alternate exemplary cross-straps of the apparatus, in accordance with at least one embodiment.

In at least one embodiment, as best illustrated in FIG. 3, the at least one first cross-strap 30 comprises a first anterior strap portion 48 and a spaced apart first posterior strap portion 50, while the at least one second cross-strap 32 comprises a second anterior strap portion 52 and a spaced apart second posterior strap portion 54. Thus, in at least one such embodiment, the first anterior strap portion 48, first posterior strap portion 50, second anterior strap portion 52 and second posterior strap portion 54 are four separate straps. However, in at least one alternate embodiment, as best illustrated in FIG. 4, the first posterior strap portion 50 and second posterior strap portion 54 are integral with or otherwise secured to one another. In at least one such embodiment, where the first posterior strap portion 50 is integral with the second posterior strap portion 54, the first posterior strap portion 50 and second posterior strap portion 54 are folded against one another. Additionally, in at least one such embodiment, the first posterior strap portion 50 and second posterior strap portion 54 are joined by a connector 56 (such as a rivet, for example) configured for allowing the first posterior strap portion 50 and second posterior strap portion 54 to selectively pivot relative to one another, thereby allowing for independent movement of the first posterior strap portion 50 and second posterior strap portion 54 while substantially maintaining their general arrangement relative to one another. Similarly, in at least one further alternate embodiment (not shown), the first anterior strap portion 48 and second anterior strap portion 52 are integral with or otherwise secured to one another. In at least one such embodiment, where the first anterior strap portion 48 is integral with the second anterior strap portion 52, the first anterior strap portion 48 and second anterior strap portion 52 are folded against one another. Additionally, in at least one such embodiment, the first anterior strap portion 48 and second anterior strap portion 52 are joined by a connector 56 configured for allowing the first anterior strap portion 48 and second anterior strap portion 52 to selectively pivot relative to one another, thereby allowing for independent movement of the first anterior strap portion 48 and second anterior strap portion 52 while substantially maintaining their general arrangement relative to one another. It should be noted that the specific sizes, shapes, dimensions and relative positions of each of the first anterior strap portion 48, first posterior strap portion 50, second anterior strap portion 52 and second posterior strap portion 54 depicted in the drawings are merely illustrative, such that in further embodiments, each of the first anterior strap portion 48, first posterior strap portion 50, second anterior strap portion 52 and second posterior strap portion 54 may take on any other sizes, shapes, dimensions and/or relative positions now known or later developed—dependent at least in part on the type of brace 22 with which the apparatus 20 is engaged—so long as the apparatus 20 is capable of substantially carrying out the functionality described herein.

In at least one embodiment, the apparatus 20 further provides an at least one tensioning mechanism 58 configured for selectively urging each of the first anterior strap portion 48, first posterior strap portion 50, second anterior strap portion 52 and second posterior strap portion 54 closer together, as discussed further below. In at least one embodiment, the tensioning mechanism 58 is a rotary ratchet mechanism; however, in further embodiments, any other mechanism (or combination of mechanisms) now known or later developed, capable of selectively urging each of the first anterior strap portion 48, first posterior strap portion 50, second anterior strap portion 52 and second posterior strap portion 54 closer together, may be substituted. In at least one embodiment, the at least one tensioning mechanism 58 is positioned on a terminal end 60 of one of the first anterior strap portion 48, first posterior strap portion 50, second anterior strap portion 52 or second posterior strap portion 54. However, in further embodiments, the at least one tensioning mechanism 58 may be positioned elsewhere—either on one of the first or second cross-straps 30 or 32, or elsewhere on the apparatus 20, or even on the brace 22. In that regard, it should be noted that the specific size, shape, dimensions, type, quantity and relative position of the at least one tensioning mechanism 58 depicted in the drawings is merely illustrative, such that in further embodiments, the at least one tensioning mechanism 58 may take on any other sizes, shapes, dimensions, types, quantities and/or relative positions now known or later developed, so long as the apparatus 20 is capable of substantially carrying out the functionality described herein.

In at least one embodiment, a terminal end 60 of each of the first anterior strap portion 48, first posterior strap portion 50, second anterior strap portion 52 and second posterior strap portion 54 provides a cord channel 62 configured for allowing a cord 64 from the tensioning mechanism 58 to extend therethrough in series. In at least one such embodiment, where the at least one tensioning mechanism 58 is positioned on the terminal end 60 of one of the first anterior strap portion 48, first posterior strap portion 50, second anterior strap portion 52 or second posterior strap portion 54, the at least one tensioning mechanism 58 provides the cord channel 62 for the corresponding one of the first anterior strap portion 48, first posterior strap portion 50, second anterior strap portion 52 or second posterior strap portion 54. Thus, as illustrated best in FIGS. 3 and 4, the cord 64 from the at least one tensioning mechanism 58 extends through each of the cord channels 62 in series and forms a complete loop. As a result, during use of the apparatus 20 and corresponding brace 22, as the at least one tensioning mechanism 58 is selectively tightened, the cord 64 urges each of the first anterior strap portion 48, first posterior strap portion 50, second anterior strap portion 52 and second posterior strap portion 54 closer together. It should be noted that the specific sizes, shapes, dimensions and relative positions of each of the cord channels 62 depicted in the drawings are merely illustrative, such that in further embodiments, each of the at least one cord channels 62 may take on any other sizes, shapes, dimensions and/or relative positions now known or later developed, so long as the apparatus 20 is capable of substantially carrying out the functionality described herein.

In at least one embodiment, as illustrated best in FIGS. 3 and 4, the first anterior strap portion 48 is interconnected with the first posterior strap portion 50 by a first tether 66 sized and configured for preventing the first anterior strap portion 48 and first posterior strap portion 50 from separating too far from one another during use of the apparatus 20. Similarly, in at least one embodiment, the second anterior strap portion 52 is interconnected with the second posterior strap portion 54 by a second tether 68 sized and configured for preventing the second anterior strap portion 52 and second posterior strap portion 54 from separating too far from one another during use of the apparatus 20. Accordingly, in at least one such embodiment, the second tether 68 is substantially transversely oriented relative to the first tether 66 and positioned for intersecting the first tether 66 in an overlapping fashion at the cross-strap intersection 34 substantially at the user's joint 26. In at least one embodiment, the first tether 66 is engaged proximal the terminal ends 60 of each of the first anterior strap portion 48 and first posterior strap portion 50, and the second tether 68 is engaged proximal the terminal ends 60 of each of the second anterior strap portion 52 and second posterior strap portion 54. However, in further embodiments, each of the first and second tethers 66 and 68 may be engaged elsewhere on the respective first anterior strap portion 48, first posterior strap portion 50, second anterior strap portion 52 and second posterior strap portion 54. In at least one embodiment the first and second tethers 66 and 68 are constructed out of an elastic or otherwise resilient material, which allows for independent movement of the first anterior strap portion 48, first posterior strap portion 50, second anterior strap portion 52 and second posterior strap portion 54 as the user moves the joint 26, while always biasing the first anterior strap portion 48, first posterior strap portion 50, second anterior strap portion 52 and second posterior strap portion 54 back into their original, neutral positions. It should be noted that the specific sizes, shapes, dimensions and relative positions of each of the first and second tethers 66 and 68 depicted in the drawings are merely illustrative, such that in further embodiments, each of the first and second tethers 66 and 68 may take on any other sizes, shapes, dimensions and/or relative positions now known or later developed—dependent at least in part on the type of brace 22 with which the apparatus 20 is engaged—so long as the apparatus 20 is capable of substantially carrying out the functionality described herein.

Figure 5:
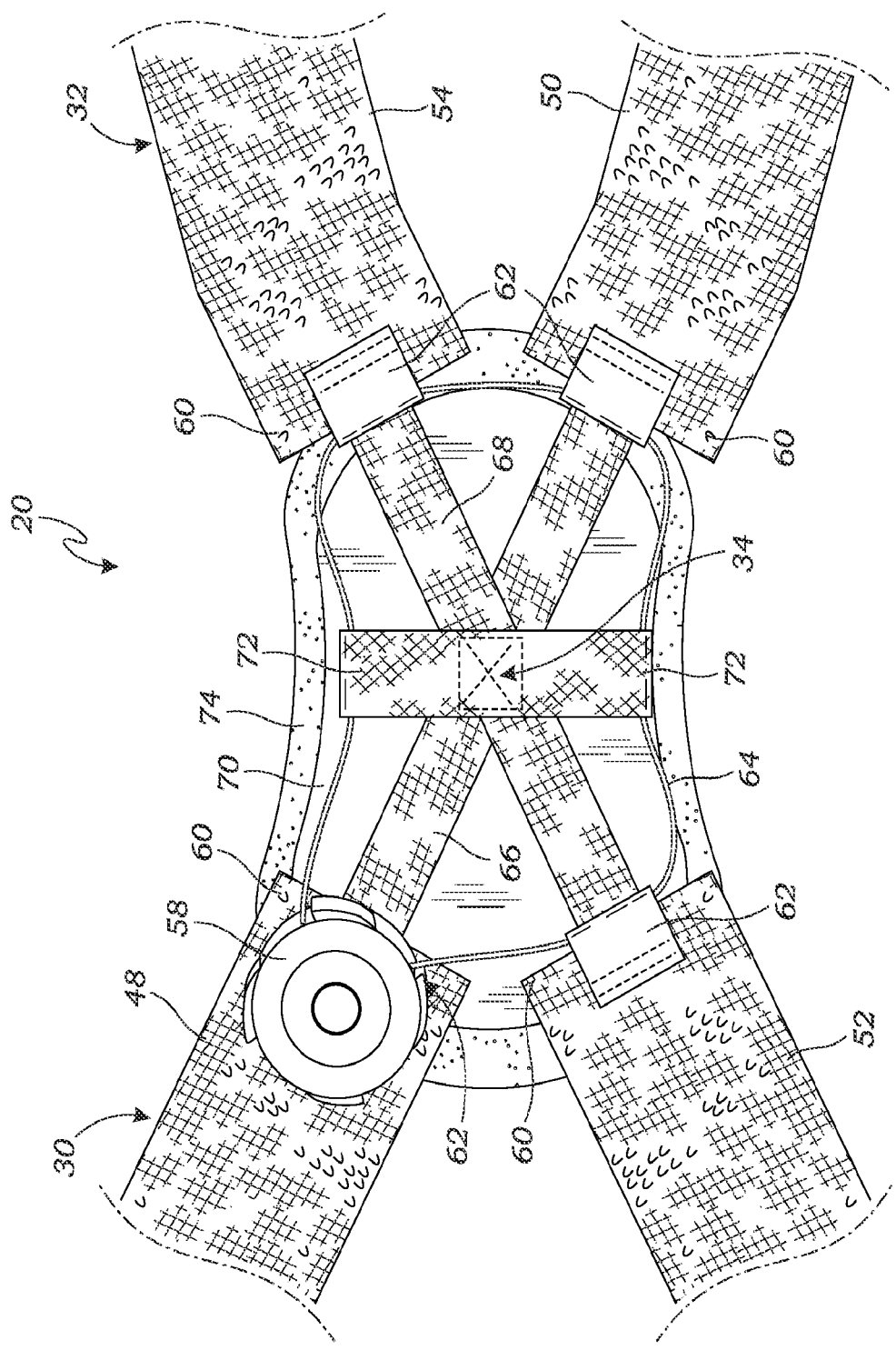
FIG. 5 is a partial top plan view of an exemplary embodiment of the apparatus with a cover portion omitted, in accordance with at least one embodiment.

In at least one embodiment, as best illustrated in FIG. 5, the apparatus 20 further provides a mounting plate 70 positioned adjacent to the first and second tethers 66 and 68 substantially at the cross-strap intersection 34. In at least one such embodiment, the first and second tethers 66 and 68 are secured to the mounting plate 70, substantially at the cross-strap intersection 34, using stitching, adhesive, welding, or any other technique—now known or later developed—capable of securing the first and second tethers 66 and 68 to the mounting plate 70. As a result, in such embodiments, the mounting plate 70 assists in resiliently maintaining the position of the cross-strap intersection 34 relative to the first and second tethers 66 and 68 and, in turn, the first and second cross-straps 30 and 32, which allows for independent movement of the first and second cross-straps 30 and 32 as the user moves the joint 26, while always biasing the first and second cross-straps 30 and 32 back into their original positions. In other words, in at least one embodiment, the apparatus 20 acts as a locator to find a center of rotation of the joint 26 for ease of use. Additionally, in at least one embodiment, the mounting plate 70 provides an at least one additional cord channel 72 positioned and configured for allowing the cord 64 from the tensioning mechanism 58 to extend therethrough in series, along with the cord channels 62 provided by each of the first anterior strap portion 48, first posterior strap portion 50, second anterior strap portion 52 and second posterior strap portion 54, thereby assisting in maintaining the cord 64 in a proper position during use of the apparatus 20. It should be noted that the specific sizes, shapes, dimensions and relative positions of each of the at least one additional cord channel 72 depicted in the drawings are merely illustrative, such that in further embodiments, each of the at least one additional cord channel 72 may take on any other sizes, shapes, dimensions and/or relative positions now known or later developed—dependent at least in part on the type of brace 22 with which the apparatus 20 is engaged—so long as the apparatus 20 is capable of substantially carrying out the functionality described herein. Similarly, the specific size, shape, dimensions and relative position of the mounting plate 70 depicted in the drawings is merely illustrative, such that in further embodiments, the mounting plate 70 may take on any other sizes, shapes, dimensions and/or relative positions now known or later developed —dependent at least in part on the type of brace 22 with which the apparatus 20 is engaged—so long as the apparatus 20 is capable of substantially carrying out the functionality described herein. In at least one embodiment, the mounting plate 70 is constructed out of a semi-flexible rubber or other resilient material. However, in further embodiments, the mounting plate 70 may be constructed out of any other material (or combination of materials) now known or later developed, so long as the apparatus 20 is capable of substantially carrying out the functionality described herein.

In at least one embodiment, with continued reference to FIG. 5, the apparatus 20 further provides a mounting plate pad 74 positioned adjacent to a rear surface of the mounting plate 70, substantially between the mounting plate 70 and the user's joint 26, so as to provide added comfort during use of the apparatus 20. In at least one such embodiment, the mounting plate pad 74 is constructed out of a soft and/or padded material, such as foam, for example. However, in further embodiments, the mounting plate pad 74 may be constructed out of any other material (or combination of materials) now known or later developed, so long as the apparatus 20 is capable of substantially carrying out the functionality described herein. Additionally, the mounting plate pad 74 may take on any other sizes, shapes, dimensions and/or relative positions now known or later developed—dependent at least in part on the size, shape, dimensions and relative position of the corresponding mounting plate 70—so long as the apparatus 20 is capable of substantially carrying out the functionality described herein.

Figure 6:
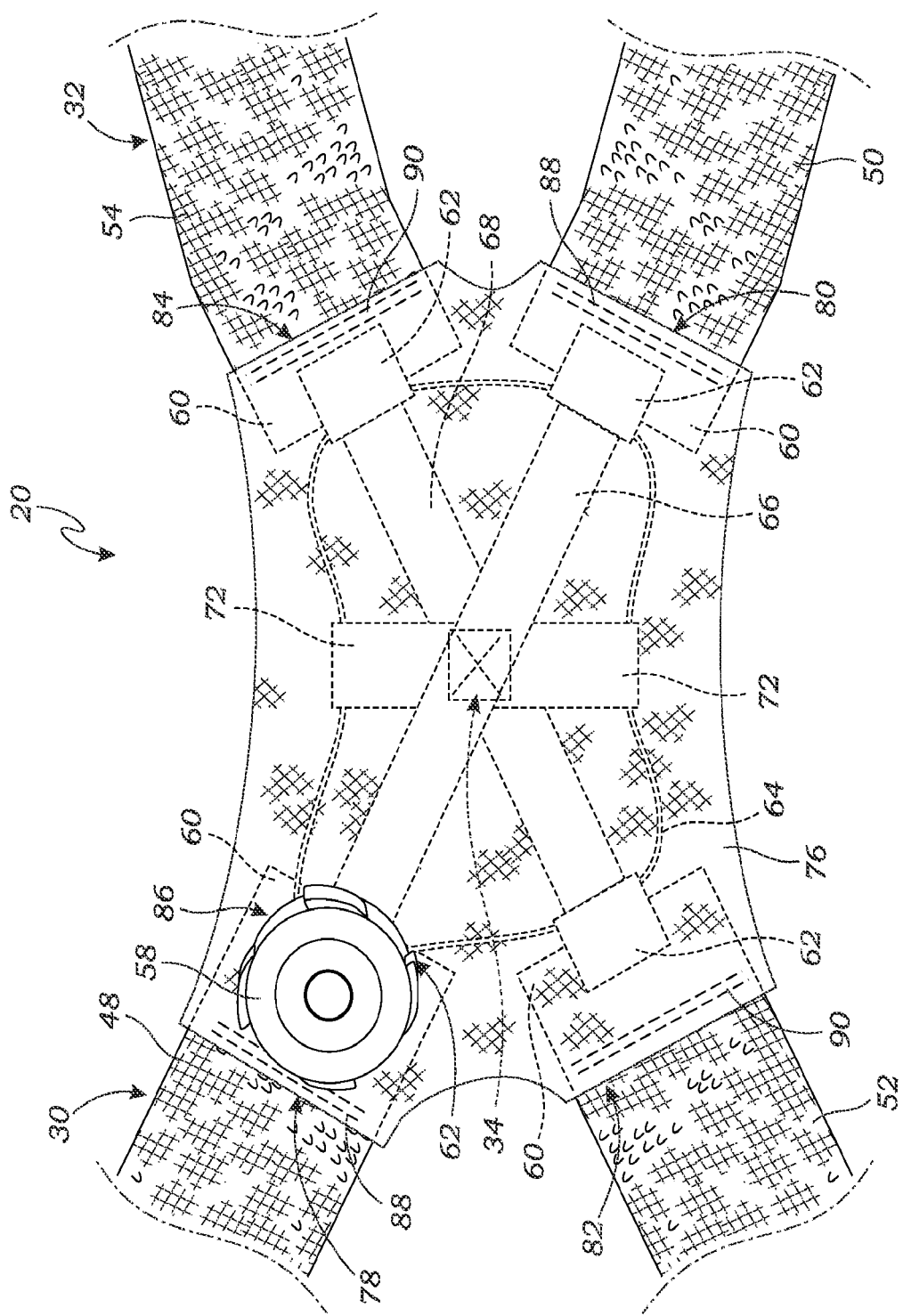
FIG. 6 is a partial top plan view thereof, with an exemplary cover portion of the apparatus included, in accordance with at least one embodiment.

In at least one embodiment, as best illustrated in FIGS. 2 and 6, the apparatus 20 further provides a cover portion 76 sized and configured for substantially encasing (or otherwise covering) the terminal ends 60 of each of the first anterior strap portion 48, first posterior strap portion 50, second anterior strap portion 52 and second posterior strap portion 54 (along with each of the first and second tethers 66 and 68, in at least one embodiment) therewithin. In at least one embodiment, where the apparatus 20 provides a mounting plate 70 and mounting plate pad 74, the cover portion 76 is sized and configured for substantially encasing (or otherwise covering) each of the mounting plate 70 and mounting plate pad 74 therewithin as well. Additionally, in at least one embodiment, the cover portion 76 is constructed out of a resilient material such as fabric, silicone, rubber, soft plastic, or any other material (or combination of materials)—now known or later developed—having sufficient elastic properties for allowing the cover portion 76 to substantially carry out the functionality described herein. In at least one alternate embodiment, the cover portion 76 may be constructed out of a non-resilient material. In at least one embodiment, the cover portion 76 provides a first anterior strap aperture 78 positioned and configured for allowing the terminal end 60 of the first anterior strap portion 48 to extend therethrough, a first posterior strap aperture 80 positioned and configured for allowing the terminal end 60 of the first posterior strap portion 50 to extend therethrough, a second anterior strap aperture 82 positioned and configured for allowing the terminal end 60 of the second anterior strap portion 52 to extend therethrough, and a second posterior strap aperture 84 positioned and configured for allowing the terminal end 60 of the second posterior strap portion 54 to extend therethrough. In at least one embodiment, the cover portion 76 further provides an at least one tensioning aperture 86 positioned and configured for allowing the at least one tensioning mechanism 58 to extend therethrough. Accordingly, the specific size, shape and dimensions of the cover portion 76 are dependent at least in part on the sizes, shapes, dimensions, quantities and relative positions of the various components of the apparatus 20. Thus, the cover portion 76 depicted in the drawings is merely exemplary.

In at least one embodiment, the cover portion 76 provides an at least one first engagement mechanism 88 positioned and configured for engagement with the first cross-strap 30, and an at least one second engagement mechanism 90 positioned and configured for engagement with the second cross-strap 32, thereby maintaining the position of the cover portion 76 relative to the cross-strap intersection 34 so that the cross-strap intersection 34 is unable to substantially move relative to the cover portion 76. In at least one embodiment, as best illustrated in FIG. 6, the cover portion 76 provides a pair of first engagement mechanisms 88 positioned on opposing edges of the cover portion 76 proximal the first anterior strap aperture 78 and first posterior strap aperture 80, along with a pair of second engagement mechanisms 90 positioned on further opposing edges of the cover portion 76 proximal the second anterior strap aperture 82 and second posterior strap aperture 84. In at least one embodiment, each of the first and second engagement mechanisms 88 and 90 is a permanent engagement mechanism, such as stitching or adhesive for example. In at least one alternate embodiment, each of the first and second engagement mechanisms 88 and 90 is a non-permanent engagement mechanism positioned and configured for mating with corresponding non-permanent engagement mechanisms provided by each of the first and second cross-straps 30 and 32, such as hook-and-loop fasteners, buttons, snaps or magnets for example. It should be noted that the specific sizes, shapes, dimensions, types, quantities and relative positions of the first and second engagement mechanisms 88 and 90 as depicted in the drawings are merely exemplary and are shown for illustrative purposes. In further embodiments, the first and second engagement mechanisms 88 and 90 may take on any other sizes, shapes, dimensions, types, quantities and/or relative positions—now known or later developed—capable of allowing the apparatus 20 to substantially carry out the functionality described herein. In at least one such further embodiment, the first and second engagement mechanisms 88 and 90 are one and the same—i.e., a single engagement mechanism positioned and configured for engagement with each of the first and second cross straps 30 and 32, thereby maintaining the position of the cover portion 76 relative to the cross-strap intersection 34 so that the cross-strap intersection 34 is unable to substantially move relative to the cover portion 76. In at least one further embodiment, the first and second tethers 66 and 68 may be omitted, such that the cover portion 76 performs the functionality of the first and second tethers 66 and 68 instead. In at least one such further embodiment, the cover portion 76 is configured similar to the resilient hub portion described in Applicant's international application number PCT/US2021/016489, the contents of which are incorporated herein by reference.

Accordingly, in at least one embodiment, the apparatus 20 is capable of allowing for independent movement of the first and second cross-straps 30 and 32 while maintaining a load directly across a center of the user's joint 26 during movement of the joint 26. Thus, in at least one embodiment, where the brace 22 is a knee brace, the apparatus 20 is capable of offloading the knee joint 26 to relieve unicompartmental osteoarthritis; though it may also be used for other purposes, such as for preventing elbow or knee hyperextension, or scoliosis stability for example.

Aspects of the present specification may also be described as the following embodiments:

1. A cross-strap tensioning apparatus for use with a brace, the brace having a proximal portion engageable above a joint of a user and an opposing distal portion engageable below the joint, the apparatus comprising: an at least one first cross-strap and an at least one second cross-strap each extending between and interconnecting the proximal and distal portions of the brace, the first and second cross-straps substantially transversely oriented relative to one another and positioned for intersecting one another in an overlapping fashion at a cross-strap intersection substantially at the joint; the at least one first cross-strap comprising: a first anterior strap portion; and a first posterior strap portion spaced apart from the first anterior strap portion; the at least one second cross-strap comprising: a second anterior strap portion; and a second posterior strap portion spaced apart from the second anterior strap portion; an at least one tensioning mechanism configured for selectively urging each of the first anterior strap portion, first posterior strap portion, second anterior strap portion and second posterior strap portion closer together; and a terminal end of each of the first anterior strap portion, first posterior strap portion, second anterior strap portion and second posterior strap portion providing a cord channel configured for allowing a cord from the at least one tensioning mechanism to extend therethrough in series; whereby, during use of the apparatus, as the at least one tensioning mechanism is selectively tightened, the cord urges each of the first anterior strap portion, first posterior strap portion, second anterior strap portion and second posterior strap portion closer together.

2. The cross-strap tensioning apparatus according to embodiment 1, wherein each of the at least one first cross-strap and second cross-strap is removably engaged with the proximal and distal portions of the brace.

3. The cross-strap tensioning apparatus according to embodiments 1-2, wherein the first posterior strap portion of the at least one first cross-strap and the second posterior strap portion of the at least one second cross-strap are joined by a connector.

4. The cross-strap tensioning apparatus according to embodiments 1-3, wherein the first anterior strap portion of the at least one first cross-strap and the second anterior strap portion of the at least one second cross-strap are joined by a connector.

5. The cross-strap tensioning apparatus according to embodiments 1-4, wherein the at least one tensioning mechanism is a rotary ratchet mechanism.

6. The cross-strap tensioning apparatus according to embodiments 1-5, wherein the at least one tensioning mechanism is positioned on the terminal end of one of the first anterior strap portion, first posterior strap portion, second anterior strap portion or second posterior strap portion.

7. The cross-strap tensioning apparatus according to embodiments 1-6, further comprising: a first tether extending between and interconnecting the first anterior strap portion and the first posterior strap portion of the at least one first cross-strap; and a second tether extending between and interconnecting the second anterior strap portion and the second posterior strap portion of the at least one second cross-strap; whereby the first and second tethers are substantially transversely oriented relative to one another and positioned for intersecting one another in an overlapping fashion at the cross-strap intersection.

8. The cross-strap tensioning apparatus according to embodiments 1-7, wherein: the first tether is engaged proximal the terminal ends of each of the first anterior strap portion and first posterior strap portion of the at least one first cross-strap; and the second tether is engaged proximal the terminal ends of each of the second anterior strap portion and second posterior strap portion of the at least one second cross-strap.

9. The cross-strap tensioning apparatus according to embodiments 1-8, wherein the first and second tethers are constructed out of an elastic or otherwise resilient material.

10. The cross-strap tensioning apparatus according to embodiments 1-9, further comprising a mounting plate on which the first and second tethers are secured in a location substantially at the cross-strap intersection.

11. The cross-strap tensioning apparatus according to embodiments 1-10, wherein the mounting plate provides an at least one additional cord channel positioned and configured for allowing the cord from the at least one tensioning mechanism to extend therethrough in series, along with the cord channels provided by each of the first anterior strap portion, first posterior strap portion, second anterior strap portion and second posterior strap portion.

12. The cross-strap tensioning apparatus according to embodiments 1-11, wherein the mounting plate is constructed out of a semi-flexible rubber or other resilient material.

13. The cross-strap tensioning apparatus according to embodiments 1-12, further comprising a mounting plate pad positioned adjacent to a rear surface of the mounting plate, substantially between the mounting plate and the user's joint.

14. The cross-strap tensioning apparatus according to embodiments 1-13, wherein the mounting plate pad is constructed out of a soft and/or padded material.

15. The cross-strap tensioning apparatus according to embodiments 1-14, further comprising a cover portion sized and configured for substantially encasing or otherwise covering the terminal ends of each of the first anterior strap portion, first posterior strap portion, second anterior strap portion and second posterior strap portion therewithin, the cover portion providing: a first anterior strap aperture positioned and configured for allowing the terminal end of the first anterior strap portion to extend therethrough; a first posterior strap aperture positioned and configured for allowing the terminal end of the first posterior strap portion to extend therethrough; a second anterior strap aperture positioned and configured for allowing the terminal end of the second anterior strap portion to extend therethrough; a second posterior strap aperture positioned and configured for allowing the terminal end of the second posterior strap portion to extend therethrough; an at least one first engagement mechanism positioned and configured for engagement with the first cross-strap proximal the cross-strap intersection; and an at least one second engagement mechanism positioned and configured for engagement with the second cross-strap proximal the cross-strap intersection.

16. The cross-strap tensioning apparatus according to embodiments 1-15, wherein: the cover portion provides a pair of first engagement mechanisms positioned on opposing edges of the cover portion proximal the first anterior strap aperture and first posterior strap aperture; and the cover portion further provides a pair of second engagement mechanisms positioned on further opposing edges of the cover portion proximal the second anterior strap aperture and second posterior strap aperture.

17. The cross-strap tensioning apparatus according to embodiments 1-16, wherein each of the first and second engagement mechanisms is a permanent engagement mechanism.

18. The cross-strap tensioning apparatus according to embodiments 1-17, wherein each of the first and second engagement mechanisms is a non-permanent engagement mechanism.

19. The cross-strap tensioning apparatus according to embodiments 1-18, wherein the cover portion further provides an at least one tensioning aperture positioned and configured for allowing the at least one tensioning mechanism to extend therethrough.

20. The cross-strap tensioning apparatus according to embodiments 1-19, wherein the cover portion is constructed out of a resilient material.

21. A cross-strap tensioning apparatus for use with a brace, the brace having a proximal portion engageable above a joint of a user and an opposing distal portion engageable below the joint, the apparatus comprising: an at least one first cross-strap and an at least one second cross-strap each extending between and interconnecting the proximal and distal portions of the brace, the first and second cross-straps substantially transversely oriented relative to one another and positioned for intersecting one another in an overlapping fashion at a cross-strap intersection substantially at the joint; the at least one first cross-strap comprising: a first anterior strap portion; a first posterior strap portion spaced apart from the first anterior strap portion; and a resilient first tether extending between and interconnecting a terminal end of the first anterior strap portion and a terminal end of the first posterior strap portion; the at least one second cross-strap comprising: a second anterior strap portion; a second posterior strap portion spaced apart from the second anterior strap portion; and a resilient second tether extending between and interconnecting a terminal end of the second anterior strap portion and a terminal end of the second posterior strap portion, the second tether substantially transversely oriented relative to the first tether and positioned for intersecting the first tether in an overlapping fashion at the cross-strap intersection; an at least one tensioning mechanism configured for selectively urging each of the first anterior strap portion, first posterior strap portion, second anterior strap portion and second posterior strap portion closer together; and the terminal end of each of the first anterior strap portion, first posterior strap portion, second anterior strap portion and second posterior strap portion providing a cord channel configured for allowing a cord from the at least one tensioning mechanism to extend therethrough in series; whereby, during use of the apparatus, as the at least one tensioning mechanism is selectively tightened, the cord urges each of the first anterior strap portion, first posterior strap portion, second anterior strap portion and second posterior strap portion closer together.

22. A cross-strap tensioning apparatus for use with a brace, the brace having a proximal portion engageable above a joint of a user and an opposing distal portion engageable below the joint, the apparatus comprising: an at least one first cross-strap and an at least one second cross-strap each extending between and interconnecting the proximal and distal portions of the brace, the first and second cross-straps substantially transversely oriented relative to one another and positioned for intersecting one another in an overlapping fashion at a cross-strap intersection substantially at the joint; the at least one first cross-strap comprising: a first anterior strap portion; and a first posterior strap portion spaced apart from the first anterior strap portion; the at least one second cross-strap comprising: a second anterior strap portion; and a second posterior strap portion spaced apart from the second anterior strap portion; an at least one tensioning mechanism configured for selectively urging each of the first anterior strap portion, first posterior strap portion, second anterior strap portion and second posterior strap portion closer together; a terminal end of each of the first anterior strap portion, first posterior strap portion, second anterior strap portion and second posterior strap portion providing a cord channel configured for allowing a cord from the at least one tensioning mechanism to extend therethrough in series; a resilient cover portion sized and configured for substantially encasing or otherwise covering the terminal ends of each of the first anterior strap portion, first posterior strap portion, second anterior strap portion and second posterior strap portion therewithin, the cover portion providing: a first anterior strap aperture positioned and configured for allowing the terminal end of the first anterior strap portion to extend therethrough; a first posterior strap aperture positioned and configured for allowing the terminal end of the first posterior strap portion to extend therethrough; a second anterior strap aperture positioned and configured for allowing the terminal end of the second anterior strap portion to extend therethrough; a second posterior strap aperture positioned and configured for allowing the terminal end of the second posterior strap portion to extend therethrough; an at least one first engagement mechanism positioned and configured for engagement with the first cross-strap proximal the cross-strap intersection; and an at least one second engagement mechanism positioned and configured for engagement with the second cross-strap proximal the cross-strap intersection; whereby, during use of the apparatus, as the at least one tensioning mechanism is selectively tightened, the cord urges each of the first anterior strap portion, first posterior strap portion, second anterior strap portion and second posterior strap portion closer together.

23. A combination cross-strap tensioning apparatus and brace comprising: a brace having a proximal portion engageable above a joint of a user and an opposing distal portion engageable below the joint; and a cross-strap tensioning apparatus comprising: an at least one first cross-strap and an at least one second cross-strap each extending between and interconnecting the proximal and distal portions of the brace, the first and second cross-straps substantially transversely oriented relative to one another and positioned for intersecting one another in an overlapping fashion at a cross-strap intersection substantially at the joint; the at least one first cross-strap comprising: a first anterior strap portion; and a first posterior strap portion spaced apart from the first anterior strap portion; the at least one second cross-strap comprising: a second anterior strap portion; and a second posterior strap portion spaced apart from the second anterior strap portion; an at least one tensioning mechanism configured for selectively urging each of the first anterior strap portion, first posterior strap portion, second anterior strap portion and second posterior strap portion closer together; and a terminal end of each of the first anterior strap portion, first posterior strap portion, second anterior strap portion and second posterior strap portion providing a cord channel configured for allowing a cord from the at least one tensioning mechanism to extend therethrough in series; whereby, during use of the apparatus, as the at least one tensioning mechanism is selectively tightened, the cord urges each of the first anterior strap portion, first posterior strap portion, second anterior strap portion and second posterior strap portion closer together.

24. The combination cross-strap tensioning apparatus and brace according to embodiment 23, wherein each of the at least one first cross-strap and second cross-strap is removably engaged with the proximal and distal portions of the brace.

25. The combination cross-strap tensioning apparatus and brace according to embodiments 23-24, wherein the first posterior strap portion of the at least one first cross-strap and the second posterior strap portion of the at least one second cross-strap are joined by a connector.

26. The combination cross-strap tensioning apparatus and brace according to embodiments 23-25, wherein the first anterior strap portion of the at least one first cross-strap and the second anterior strap portion of the at least one second cross-strap are joined by a connector.

27. The combination cross-strap tensioning apparatus and brace according to embodiments 23-26, wherein the at least one tensioning mechanism is a rotary ratchet mechanism.

28. The combination cross-strap tensioning apparatus and brace according to embodiments 23-27, wherein the at least one tensioning mechanism is positioned on the terminal end of one of the first anterior strap portion, first posterior strap portion, second anterior strap portion or second posterior strap portion.

29. The combination cross-strap tensioning apparatus and brace according to embodiments 23-28, further comprising: a first tether extending between and interconnecting the first anterior strap portion and the first posterior strap portion of the at least one first cross-strap; and a second tether extending between and interconnecting the second anterior strap portion and the second posterior strap portion of the at least one second cross-strap; whereby the first and second tethers are substantially transversely oriented relative to one another and positioned for intersecting one another in an overlapping fashion at the cross-strap intersection.

30. The combination cross-strap tensioning apparatus and brace according to embodiments 23-29, wherein: the first tether is engaged proximal the terminal ends of each of the first anterior strap portion and first posterior strap portion of the at least one first cross-strap; and the second tether is engaged proximal the terminal ends of each of the second anterior strap portion and second posterior strap portion of the at least one second cross-strap.

31. The combination cross-strap tensioning apparatus and brace according to embodiments 23-30, wherein the first and second tethers are constructed out of an elastic or otherwise resilient material.

32. The combination cross-strap tensioning apparatus and brace according to embodiments 23-31, further comprising a mounting plate on which the first and second tethers are secured in a location substantially at the cross-strap intersection.

33. The combination cross-strap tensioning apparatus and brace according to embodiments 23-32, wherein the mounting plate provides an at least one additional cord channel positioned and configured for allowing the cord from the at least one tensioning mechanism to extend therethrough in series, along with the cord channels provided by each of the first anterior strap portion, first posterior strap portion, second anterior strap portion and second posterior strap portion.

34. The combination cross-strap tensioning apparatus and brace according to embodiments 23-33, wherein the mounting plate is constructed out of a semi-flexible rubber or other resilient material.

35. The combination cross-strap tensioning apparatus and brace according to embodiments 23-34, further comprising a mounting plate pad positioned adjacent to a rear surface of the mounting plate, substantially between the mounting plate and the user's joint.

36. The combination cross-strap tensioning apparatus and brace according to embodiments 23-35, wherein the mounting plate pad is constructed out of a soft and/or padded material.

37. The combination cross-strap tensioning apparatus and brace according to embodiments 23-36, further comprising a cover portion sized and configured for substantially encasing or otherwise covering the terminal ends of each of the first anterior strap portion, first posterior strap portion, second anterior strap portion and second posterior strap portion therewithin, the cover portion providing: a first anterior strap aperture positioned and configured for allowing the terminal end of the first anterior strap portion to extend therethrough; a first posterior strap aperture positioned and configured for allowing the terminal end of the first posterior strap portion to extend therethrough; a second anterior strap aperture positioned and configured for allowing the terminal end of the second anterior strap portion to extend therethrough; a second posterior strap aperture positioned and configured for allowing the terminal end of the second posterior strap portion to extend therethrough; an at least one first engagement mechanism positioned and configured for engagement with the first cross-strap proximal the cross-strap intersection; and an at least one second engagement mechanism positioned and configured for engagement with the second cross-strap proximal the cross-strap intersection.

38. The combination cross-strap tensioning apparatus and brace according to embodiments 23-37, wherein: the cover portion provides a pair of first engagement mechanisms positioned on opposing edges of the cover portion proximal the first anterior strap aperture and first posterior strap aperture; and the cover portion further provides a pair of second engagement mechanisms positioned on further opposing edges of the cover portion proximal the second anterior strap aperture and second posterior strap aperture.

39. The combination cross-strap tensioning apparatus and brace according to embodiments 23-38, wherein each of the first and second engagement mechanisms is a permanent to engagement mechanism.

40. The combination cross-strap tensioning apparatus and brace according to embodiments 23-39, wherein each of the first and second engagement mechanisms is a non-permanent engagement mechanism.

41. The combination cross-strap tensioning apparatus and brace according to embodiments 23-40, wherein the cover portion further provides an at least one tensioning aperture positioned and configured for allowing the at least one tensioning mechanism to extend therethrough.

42. The combination cross-strap tensioning apparatus and brace according to embodiments 23-41, wherein the cover portion is constructed out of a resilient material.

In closing, regarding the exemplary embodiments of the present invention as shown and described herein, it will be appreciated that an osteoarthritis brace incorporating a cross-strap tensioning apparatus is disclosed. Because the principles of the invention may be practiced in a number of configurations beyond those shown and described, it is to be understood that the invention is not in any way limited by the exemplary embodiments, but is generally directed to an osteoarthritis brace incorporating a cross-strap tensioning apparatus and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As is such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that any methods and the order in which the respective elements of each method are performed are purely exemplary. Depending on the implementation, they may be performed in any order or in parallel, unless indicated otherwise in the present disclosure.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A cross-strap tensioning apparatus for use with a brace, the brace having a proximal portion engageable above a joint of a user and an opposing distal portion engageable below the joint, the apparatus comprising:
    an at least one first cross-strap and an at least one second cross-strap each extending between and interconnecting the proximal and distal portions of the brace, the first and second cross-straps transversely oriented relative to one another and positioned for intersecting one another in an overlapping fashion at a cross-strap intersection at the joint;
    the at least one first cross-strap comprising:
        a first anterior strap portion; and
        a first posterior strap portion spaced apart from the first anterior strap portion;
    the at least one second cross-strap comprising:
        a second anterior strap portion; and
        a second posterior strap portion spaced apart from the second anterior strap portion;
    an at least one tensioning mechanism configured for selectively urging each of the first anterior strap portion, first posterior strap portion, second anterior strap portion and second posterior strap portion closer together; and
    a terminal end of each of the first anterior strap portion, first posterior strap portion, second anterior strap portion and second posterior strap portion providing a cord channel configured for allowing a cord from the at least one tensioning mechanism to extend therethrough in series;
    whereby, during use of the apparatus, as the at least one tensioning mechanism is selectively tightened, the cord urges each of the first anterior strap portion, first posterior strap portion, second anterior strap portion and second posterior strap portion closer together.

2. The cross-strap tensioning apparatus of claim 1, wherein each of the at least one first cross-strap and second cross-strap is removably engaged with the proximal and distal portions of the brace.

3. The cross-strap tensioning apparatus of claim 1, wherein the first posterior strap portion of the at least one first cross-strap and the second posterior strap portion of the at least one second cross-strap are joined by a connector.

4. The cross-strap tensioning apparatus of claim 1, wherein the first anterior strap portion of the at least one first cross-strap and the second anterior strap portion of the at least one second cross-strap are joined by a connector.

5. The cross-strap tensioning apparatus of claim 1, wherein the at least one tensioning mechanism is positioned on the terminal end of one of the first anterior strap portion, first posterior strap portion, second anterior strap portion or second posterior strap portion.

6. The cross-strap tensioning apparatus of claim 1, further comprising:
    a first tether extending between and interconnecting the first anterior strap portion and the first posterior strap portion of the at least one first cross-strap; and
    a second tether extending between and interconnecting the second anterior strap portion and the second posterior strap portion of the at least one second cross-strap;
    whereby the first and second tethers are transversely oriented relative to one another and positioned for intersecting one another in an overlapping fashion at the cross-strap intersection.

7. The cross-strap tensioning apparatus of claim 6, wherein:
    the first tether is engaged proximal the terminal ends of each of the first anterior strap portion and first posterior strap portion of the at least one first cross-strap; and
    the second tether is engaged proximal the terminal ends of each of the second anterior strap portion and second posterior strap portion of the at least one second cross-strap.

8. The cross-strap tensioning apparatus of claim 6, wherein the first and second tethers are constructed out of an elastic or otherwise resilient material.

9. The cross-strap tensioning apparatus of claim 6, further comprising a mounting plate on which the first and second tethers are secured in a location at the cross-strap intersection.

10. The cross-strap tensioning apparatus of claim 9, wherein the mounting plate provides an at least one additional cord channel positioned and configured for allowing the cord from the at least one tensioning mechanism to extend therethrough in series, along with the cord channels provided by each of the first anterior strap portion, first posterior strap portion, second anterior strap portion and second posterior strap portion.

11. The cross-strap tensioning apparatus of claim 9, wherein the mounting plate is constructed out of a semi-flexible rubber or other resilient material.

12. The cross-strap tensioning apparatus of claim 9, further comprising a mounting plate pad positioned adjacent to a rear surface of the mounting plate, between the mounting plate and the user's joint.

13. The cross-strap tensioning apparatus of claim 1, further comprising a cover portion sized and configured for encasing or otherwise covering the terminal ends of each of the first anterior strap portion, first posterior strap portion, second anterior strap portion and second posterior strap portion therewithin, the cover portion providing:
   a first anterior strap aperture positioned and configured for allowing the terminal end of the first anterior strap portion to extend therethrough;
   a first posterior strap aperture positioned and configured for allowing the terminal end of the first posterior strap portion to extend therethrough;
   a second anterior strap aperture positioned and configured for allowing the terminal end of the second anterior strap portion to extend therethrough;
   a second posterior strap aperture positioned and configured for allowing the terminal end of the second posterior strap portion to extend therethrough;
   an at least one first engagement mechanism positioned and configured for engagement with the first cross-strap proximal the cross-strap intersection; and
   an at least one second engagement mechanism positioned and configured for engagement with the second cross-strap proximal the cross-strap intersection.

14. The cross-strap tensioning apparatus of claim 13, wherein:
   the cover portion provides a pair of first engagement mechanisms positioned on opposing edges of the cover portion proximal the first anterior strap aperture and first posterior strap aperture; and
   the cover portion further provides a pair of second engagement mechanisms positioned on further opposing edges of the cover portion proximal the second anterior strap aperture and second posterior strap aperture.

15. The cross-strap tensioning apparatus of claim 13, wherein each of the first and second engagement mechanisms is a permanent engagement mechanism.

16. The cross-strap tensioning apparatus of claim 13, wherein each of the first and second engagement mechanisms is a non-permanent engagement mechanism.

17. The cross-strap tensioning apparatus of claim 13, wherein the cover portion further provides an at least one tensioning aperture positioned and configured for allowing the at least one tensioning mechanism to extend therethrough.

18. The cross-strap tensioning apparatus of claim 13, wherein the cover portion is constructed out of a resilient material.

19. A cross-strap tensioning apparatus for use with a brace, the brace having a proximal portion engageable above a joint of a user and an opposing distal portion engageable below the joint, the apparatus comprising:
   an at least one first cross-strap and an at least one second cross-strap each extending between and interconnecting the proximal and distal portions of the brace, the first and second cross-straps transversely oriented relative to one another and positioned for intersecting one another in an overlapping fashion at a cross-strap intersection at the joint;
   the at least one first cross-strap comprising:
      a first anterior strap portion;
      a first posterior strap portion spaced apart from the first anterior strap portion; and
      a resilient first tether extending between and interconnecting a terminal end of the first anterior strap portion and a terminal end of the first posterior strap portion;
   the at least one second cross-strap comprising:
      a second anterior strap portion;
      a second posterior strap portion spaced apart from the second anterior strap portion; and
      a resilient second tether extending between and interconnecting a terminal end of the second anterior strap portion and a terminal end of the second posterior strap portion, the second tether transversely oriented relative to the first tether and positioned for intersecting the first tether in an overlapping fashion at the cross-strap intersection;
   an at least one tensioning mechanism configured for selectively urging each of the first anterior strap portion, first posterior strap portion, second anterior strap portion and second posterior strap portion closer together; and
   the terminal end of each of the first anterior strap portion, first posterior strap portion, second anterior strap portion and second posterior strap portion providing a cord channel configured for allowing a cord from the at least one tensioning mechanism to extend therethrough in series;
   whereby, during use of the apparatus, as the at least one tensioning mechanism is selectively tightened, the cord urges each of the first anterior strap portion, first posterior strap portion, second anterior strap portion and second posterior strap portion closer together.

20. A cross-strap tensioning apparatus for use with a brace, the brace having a proximal portion engageable above a joint of a user and an opposing distal portion engageable below the joint, the apparatus comprising:
   an at least one first cross-strap and an at least one second cross-strap each extending between and interconnecting the proximal and distal portions of the brace, the first and second cross-straps transversely oriented relative to one another and positioned for intersecting one another in an overlapping fashion at a cross-strap intersection at the joint;
   the at least one first cross-strap comprising:
      a first anterior strap portion; and
      a first posterior strap portion spaced apart from the first anterior strap portion;
   the at least one second cross-strap comprising:
      a second anterior strap portion; and
      a second posterior strap portion spaced apart from the second anterior strap portion;
   an at least one tensioning mechanism configured for selectively urging each of the first anterior strap portion, first posterior strap portion, second anterior strap portion and second posterior strap portion closer together;

a terminal end of each of the first anterior strap portion, first posterior strap portion, second anterior strap portion and second posterior strap portion providing a cord channel configured for allowing a cord from the at least one tensioning mechanism to extend therethrough in series;

a resilient cover portion sized and configured for encasing or otherwise covering the terminal ends of each of the first anterior strap portion, first posterior strap portion, second anterior strap portion and second posterior strap portion therewithin, the cover portion providing:

a first anterior strap aperture positioned and configured for allowing the terminal end of the first anterior strap portion to extend therethrough;

a first posterior strap aperture positioned and configured for allowing the terminal end of the first posterior strap portion to extend therethrough;

a second anterior strap aperture positioned and configured for allowing the terminal end of the second anterior strap portion to extend therethrough;

a second posterior strap aperture positioned and configured for allowing the terminal end of the second posterior strap portion to extend therethrough;

an at least one first engagement mechanism positioned and configured for engagement with the first cross-strap proximal the cross-strap intersection; and an at least one second engagement mechanism positioned and configured for engagement with the second cross-strap proximal the cross-strap intersection;

whereby, during use of the apparatus, as the at least one tensioning mechanism is selectively tightened, the cord urges each of the first anterior strap portion, first posterior strap portion, second anterior strap portion and second posterior strap portion closer together.

* * * * *